(12) United States Patent
Couderc et al.

(10) Patent No.: US 10,900,153 B2
(45) Date of Patent: Jan. 26, 2021

(54) TWO-SIDES GRIPPING KNIT

(71) Applicant: Sofradim Production, Trévoux (FR)

(72) Inventors: Xavier Couderc, Frans (FR); Anthony Mira, Villefranche sur Saone (FR); Francoise Varone, Charnoz sur ain (FR); Yves Bayon, Lyons (FR)

(73) Assignee: SOFRADIM PRODUCTION, Trevoux (FR)

( * ) Notice: Subject to any disclaimer, the term of this patent is extended or adjusted under 35 U.S.C. 154(b) by 350 days.

(21) Appl. No.: 15/965,834

(22) Filed: Apr. 27, 2018

(65) Prior Publication Data

US 2018/0318058 A1    Nov. 8, 2018

(30) Foreign Application Priority Data

May 2, 2017    (EP) .................................... 17305487

(51) Int. Cl.
*D04B 21/12*    (2006.01)
*D04B 21/14*    (2006.01)
*A61F 2/00*    (2006.01)

(52) U.S. Cl.
CPC ............ *D04B 21/12* (2013.01); *A61F 2/0063* (2013.01); *D04B 21/14* (2013.01);
(Continued)

(58) Field of Classification Search
CPC ........ D04B 21/12; D04B 21/14; D04B 21/16; D04B 21/20; D04B 23/08; D04B 23/10;
(Continued)

(56) References Cited

U.S. PATENT DOCUMENTS 3,320,649 A * 5/1967 Naimer .................. D06C 29/00
28/161
3,718,725 A * 2/1973 Hamano ................ D04B 21/04
264/163

(Continued)

FOREIGN PATENT DOCUMENTS

DE    19832634 A1    1/2000
EP    0276890 A2    8/1988
(Continued)

OTHER PUBLICATIONS

European Search Report, Application No. 14 17 2688 dated Sep. 26, 2014.
(Continued)

*Primary Examiner* — Danny Worrell
(74) *Attorney, Agent, or Firm* — Weber Rosselli & Cannon LLP

(57) ABSTRACT

The invention relates to a knit having barbs protruding outwards from both faces obtained by knitting yarns of biocompatible material in guide-bars B2, B3 and B4 of a knitting machine, wherein the knitting patterns followed by guide-bars B2 and B3 involve at least two needles and produce an arrangement of yarns defining two faces of the knit, the knitting pattern followed by guide-bar B4 making stitches generating loops protruding outwards from each of the faces of the knit, guide-bar B4 being threaded with a hot-melt monofilament yarn, heat-setting the knit, forming barbs by cutting the loops via melting.

19 Claims, 2 Drawing Sheets

(52) U.S. Cl.
CPC .............. *A61F 2002/0068* (2013.01); *A61F 2220/0016* (2013.01); *A61F 2240/001* (2013.01); *D10B 2501/0632* (2013.01); *D10B 2509/08* (2013.01)

(58) Field of Classification Search
CPC ..... A61F 2002/0068; A61F 2220/0016; D10B 2509/08
See application file for complete search history.

(56) References Cited

U.S. PATENT DOCUMENTS

| | | | |
|---|---|---|---|
| 4,338,800 | A | 7/1982 | Matsuda |
| 4,391,106 | A | 7/1983 | Schafer et al. |
| 4,476,697 | A | 10/1984 | Schafer et al. |
| 4,709,562 | A | 12/1987 | Matsuda |
| 5,254,127 | A | 10/1993 | Wholey et al. |
| 5,254,133 | A | 10/1993 | Seid |
| 5,330,445 | A | 7/1994 | Haaga |
| 5,356,432 | A | 10/1994 | Rutkow et al. |
| 5,569,273 | A | 10/1996 | Titone et al. |
| 5,761,775 | A | 6/1998 | Legome et al. |
| 5,906,617 | A | 5/1999 | Meislin |
| 6,039,741 | A | 3/2000 | Meislin |
| 6,110,210 | A | 8/2000 | Norton et al. |
| 6,120,539 | A | 9/2000 | Eldridge et al. |
| 6,408,656 | B1 | 6/2002 | Ory et al. |
| 6,443,964 | B1 | 9/2002 | Ory et al. |
| 6,596,002 | B2 | 7/2003 | Therin et al. |
| 6,638,284 | B1 | 10/2003 | Rousseau et al. |
| 6,971,252 | B2 | 12/2005 | Therin et al. |
| 6,991,643 | B2 | 1/2006 | Saadat |
| 7,083,637 | B1 | 8/2006 | Tannhauser |
| 7,213,421 | B2 | 5/2007 | Shirasaki et al. |
| 7,275,290 | B2 * | 10/2007 | Clarner .............. A44B 18/0061 24/452 |
| 7,331,199 | B2 | 2/2008 | Ory et al. |
| 7,614,258 | B2 | 11/2009 | Cherok et al. |
| 9,445,883 | B2 * | 9/2016 | Lecuivre .................. D06C 7/00 |
| 9,839,504 | B2 * | 12/2017 | Miller .................... D04B 21/20 |
| 9,839,505 | B2 * | 12/2017 | Romuald ............. A61F 2/0063 |
| 10,349,707 | B2 * | 7/2019 | Verstraete ............ A44B 18/003 |
| 2004/0039453 | A1 | 2/2004 | Anderson et al. |
| 2004/0073235 | A1 | 4/2004 | Lund |
| 2004/0225181 | A1 | 11/2004 | Chu |
| 2006/0281967 | A1 | 12/2006 | Meneghin et al. |
| 2007/0032695 | A1 | 2/2007 | Weiser |
| 2007/0038018 | A1 | 2/2007 | Chu |
| 2007/0043255 | A1 | 2/2007 | O'Donnell |
| 2008/0081945 | A1 | 4/2008 | Toso |
| 2008/0161837 | A1 | 7/2008 | Toso et al. |
| 2008/0195231 | A1 | 8/2008 | Ory et al. |
| 2008/0208360 | A1 | 8/2008 | Meneghin et al. |
| 2008/0269548 | A1 | 10/2008 | Vecchiotti et al. |
| 2009/0036907 | A1 | 2/2009 | Bayon et al. |
| 2010/0049222 | A1 | 2/2010 | Cherok et al. |
| 2010/0299880 | A1 * | 12/2010 | Pezzoli .................. D04B 21/04 24/1 |
| 2010/0312043 | A1 | 12/2010 | Goddard |
| 2011/0230707 | A1 | 9/2011 | Roll |
| 2013/0172915 | A1 | 7/2013 | Thomas et al. |

FOREIGN PATENT DOCUMENTS

| | | | |
|---|---|---|---|
| EP | | 0719527 A1 | 7/1996 |
| EP | | 0797962 A2 | 10/1997 |
| EP | | 0827724 A2 | 3/1998 |
| EP | | 0836838 A1 | 4/1998 |
| EP | | 2229918 A1 | 9/2010 |
| EP | | 2473214 B1 | 7/2012 |
| EP | | 2473133 B1 | 4/2014 |
| EP | | 2514862 A2 | 10/2015 |
| FR | | 2744906 A1 | 8/1997 |
| FR | | 2766698 A1 | 2/1999 |
| FR | | 2779937 A1 | 12/1999 |
| WO | | 9507666 A1 | 3/1995 |
| WO | | 9603091 A1 | 2/1996 |
| WO | | 9641588 A1 | 12/1996 |
| WO | | 0181667 A1 | 11/2001 |
| WO | | 03092546 A2 | 11/2003 |
| WO | | 03105727 A1 | 12/2003 |
| WO | | 2013020076 A1 | 2/2013 |
| WO | | 2013026682 A1 | 2/2013 |
| WO | WO 2013/026682 A1 | | 2/2013 |

OTHER PUBLICATIONS

European Office Action dated Aug. 29, 2016 in corresponding European Patent Application No. 14172688.5, 5 pages.
European Office Action dated Jan. 20, 2017 in corresponding European Patent Application No. 14172688.5, 5 pages.
European Search Report for EP17305487.5 date of completion is Nov. 20, 2017 (6 pages).

* cited by examiner

TWO-SIDES GRIPPING KNIT

CROSS-REFERENCE TO RELATED APPLICATIONS

This application claims benefit of and priority to European Patent Application Serial No. 17305487.5 filed May 2, 2017, the disclosure of the above-identified application is hereby incorporated by reference in its entirety.

BACKGROUND

The present invention relates to a prosthetic porous knit with outwardly protruding barbs on each of its faces and to the method for manufacturing it. The knit of the invention may be used in particular as a two-sides fixation patch or as a wall reinforcement prosthesis, and more generally in every surgery where approximating two tissue layers is needed.

SUMMARY

The need to approximate two tissue layers may occur in various locations of the anatomy of a human body. Indeed, this need may appear further to a surgery having necessitated a dissection of said two tissue layers or whenever two layers of tissue have undergone a natural phenomenon leading to their separation.

The need to approximate two tissue layers may often happen in the vicinity of the abdominal wall.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias show themselves in the form of a bulge at the surface of the skin and are classed, for example, as umbilical or groin hernias or incisional hernias, depending on where they are located. In order to repair a hernia defect, surgeons often fit a prosthesis in place which is made of synthetic mesh and replaces or strengthens the weakened anatomical tissues. For doing so, the surgeons often need to dissect two layers of tissues of the abdominal wall.

The need to approximate two tissue layers of the abdominal wall may alternatively happen in bariatric surgery, further to the dissection of two layers of tissue in order to treat people suffering for obesity.

The need to approximate two tissue layers of the abdominal wall may further happen subsequent to a natural phenomenon such as Diastasis Recti. Diastasis Recti is the creation of a gap between the two sides, namely the right side and the left side, of the rectus abdominis muscle. The distance between the right and left rectus abdominis muscles is created by the stretching of the linea alba. Such a phenomenon may occur in premature babies where the rectus abdominis is not fully developed. Alternatively, this phenomenon may also occur in pregnant women, due to the stretching of the rectus abdominis by the growing uterus.

More generally, apart from the abdominal wall, the need to approximate two tissue layers may happen anywhere in a human body, for all biological organs, connective tissues, muscles, for which the dissection of two different layers is needed.

The dissection of two tissue layers may lead to the formation of seroma. Seroma is a pocket of clear serous fluid that sometimes develops in the body after surgery. Approximating efficiently two tissue layers which have been previously dissected may prevent the development of seroma.

It is known to approximate two layers of tissue by attaching one layer to the other by means of surgical suture threads. Anyway, suturing may be time-consuming for the surgeon. It may also create tensions and tearing within the layers of tissue. In particular, the abdominal wall is submitted to a lot of pressures, coming from all directions, such as coughing, jumping, exercising, breathing, etc . . . during the daily life of a person. Approximating two tissue layers by means of suturing may prove to be painful and very uncomfortable for the patient in the long term.

There is therefore a need for a prosthesis capable of approximating two tissue layers of the body in an efficient way, without creating tensions and tearing within the tissue layers to be approximated, while preserving the comfort of the patient.

Textile-based prostheses are well known in some fields of surgery, such as abdominal wall repair. These prostheses are generally made of biocompatible prosthetic fabric conferring them a certain conformability and they may show a number of shapes, for example rectangular, circular or oval, depending on the anatomical structure to which they are to adapt. Some of theses prostheses are made from entirely bioresorbable yarns and are intended to disappear after they have performed their reinforcing function during the period of cellular colonization and tissue rehabilitation. Others comprise non-bioresorbable yarns and are intended to remain permanently in the body of the patient.

Textile-based prostheses are usually made from an arrangement of yarns, such as porous knits which comprise openings and/or pores favoring cellular growth within the knit once the prosthesis is implanted. Some of these porous knits may comprise barbs protruding outwards from each face of the knit: these barbs constitute hooks that are able to fix themselves either in another prosthetic fabric, belonging to the same prosthesis or not, or directly in the biological tissues, for example the abdominal wall.

The document WO2013/026682 describes the production of a knit comprising barbs on each of its faces. In this document, the knit is produced using four guide-bars of a knitting machine. Anyway, it has been observed that the knit described in this document may show limited elasticity in some directions.

As seen above, the need to approximate two tissue layers may happen in various locations of the anatomy, and in particular, in locations which may be submitted to pressures coming from all directions, said pressures changing directions and intensities at all times in function of the movements of the patient. The approximated tissue layers therefore need to be able to move one with respect to the other, preferably in all directions, in a smooth way: for example, they may need to come closer to each other, to possibly overlap each other during a moment, and further on, to move away one from the other, while remaining safely attached together, in order to adapt and conform smoothly to the movements of the patient.

There is therefore a need for a porous knit capable of approximating efficiently two tissue layers while showing sufficient elasticity in all directions, preferably in the warp direction, for example under a certain load of tension, so that said approximated tissue layers are capable of smoothly adapting to multidirectional pressures generated by the movements of the patient in his daily life.

There is also a need for producing such a porous knit rapidly, in an efficient and cost-effective manner.

The applicant has found a quick and simple method of producing a porous knit having both outwardly protruding barbs on its two opposite faces and a good elasticity in all directions.

The present invention relates to a prosthetic porous knit comprising an arrangement of yarns of biocompatible material defining at least two faces for said knit, said knit being provided, on each of its faces, with barbs protruding outwards from said face, said knit being obtained by the following steps:
i) providing a warp knitting machine comprising one needle-bed comprising four guide-bars, namely guide-bar B1, guide-bar B2, guide-bar B3 and guide-bar B4,
ii) knitting on said machine the yarns of biocompatible material as follows:
Guide-bar B1 is either unthreaded or threaded with yarns of biocompatible material in which case the knitting pattern followed by guide bar B1 involves at least two needles,
Guide-bars B2 and B3 are threaded with yarns of biocompatible material, the knitting patterns followed by guide-bars B2 and B3 involving at least two needles and producing said arrangement of yarns defining said two faces of said knit,
Guide-bar B4 is threaded with a hot-melt monofilament yarn of biocompatible material, the knitting pattern followed by guide-bar B4 making stitches generating loops protruding outwards from each of the faces of said knit,
iii) heat-setting the knit obtained at ii),
iv) forming barbs by melting the loops.

Another aspect of the present invention is a method for manufacturing a prosthetic porous knit comprising an arrangement of yarns of biocompatible material defining at least two faces for said knit, said knit being provided, on each of its faces, with barbs protruding outwards from said face, said process comprising the following steps:
i) providing a warp knitting machine comprising one needle-bed comprising four guide-bars, namely guide-bar B1, guide-bar B2, guide-bar B3 and guide-bar B4,
ii) knitting on said machine the yarns of biocompatible material as follows:
Guide-bar B1 is either unthreaded or threaded with yarns of biocompatible material in which case the knitting pattern followed by guide bar B1 involves at least two needles,
Guide-bars B2 and B3 are threaded with yarns of biocompatible material, the knitting patterns followed by guide-bars B2 and B3 involving at least two needles and producing said arrangement of yarns defining said two faces of said knit,
Guide-bar B4 is threaded with a hot-melt monofilament yarn of biocompatible material, the knitting pattern followed by guide-bar B4 making stitches generating loops protruding outwards from each of the faces of said knit,
iii) heat-setting the knit obtained at ii),
iv) forming barbs by melting the loops.

Another aspect of the invention is a prosthetic porous knit comprising an arrangement of yarns of biocompatible material defining at least two faces for said knit, said knit being provided, on each of its faces, with barbs protruding outwards from said face, said knit showing a tensile breaking elongation in the warp direction of at least about 50%, preferably of at least about 70%, preferably of at least about 100%, more preferably of about 108%.

Another aspect of the invention is a prosthetic porous knit comprising an arrangement of yarns of biocompatible material defining at least two faces for said knit, said knit being provided, on each of its faces, with barbs protruding outwards from said face, said knit showing a tensile elongation under 50 N in the warp direction of at least about 30%, preferably of at least about 60%, preferably of at least about 80%, more preferably of about 85%.

In the present application, the tensile breaking elongation and the tensile elongation under 50 N in the warp direction and in the weft direction are measured according to the methods described in Example 1.

In the present application, a "prosthetic knit" is understood as a knit intended to be implanted in the human or animal body in the form of a prosthesis or any other part designed at least in part with said knit.

Within the meaning of the present invention, «porous knit» means the characteristic whereby a knit has pores, or voids, cells, holes or orifices that are open and distributed uniformly or non-uniformly on the faces of the knit and within its thickness, and that promote cellular colonization. The pores can be present in all sorts of forms, for example spheres, channels and hexagonal shapes.

The knit according to the invention has barbs on both faces and shows a good elasticity in all directions, in particular in the warp direction.

The knit of the invention can thus be fastened to biological tissues via each of its faces. The knit of the invention is therefore particularly indicated for approximating two tissue layers which have been previously separated from each other, either by dissection or subsequent to a natural phenomenon.

The knit of the invention is produced on a warp knitting machine comprising one needle-bed comprising four guide-bars, namely guide-bar B1, guide-bar B2, guide-bar B3 and guide-bar B4.

The knit of the invention is produced along the warp direction of the machine by means of three guide bars, optionally four guide-bars when guide-bar B1 is threaded, operating together and each repeating a knitting pattern defining the evolution of the yarns. The evolution of a yarn from one needle to another is called a course. The needles extend along the width of the machine, which corresponds to the weft direction of the knit produced. The knitting pattern corresponds to the smallest number of courses whereby the whole yarn evolution can be described. The knitting pattern therefore involves a determined number of needles, which corresponds to the total number of needles used for the yarn to complete its whole evolution.

In the knit and method of the invention, all guide-bars used follow a knitting pattern involving at least two needles. The resulting knit shows a good elasticity, for example observable by measuring the tensile breaking elongation and/or the tensile elongation under 50N of the knit both in the warp direction and in the weft direction. In particular, the knit of the invention is free of any chain stitch, thereby showing good elastic properties in the warp direction.

The knit of the invention may therefore be used in a surgery intended to approximate two tissue layers with great efficiency. In particular, thanks to the elasticity of the knit of the invention in the warp direction and in the weft direction, the approximated tissue layers are free to move with respect to each other, while being firmly attached to each other, thereby being capable of adapting to pressures of various directions and intensities generated by the movements of a patient in its daily life.

Alternatively, the knit of the invention can be fastened to biological tissues via one of its faces, a second prosthetic textile being able to be fastened to the opposite face of said knit, by means of these barbs. In another alternative, the knit according to the invention can be fastened, by way of its barbs, to two other textiles, one on each of its faces: it can thus be useful for joining two textiles without the need to use staples.

Moreover, the manufacture of the knit according to the invention can be performed in a single knitting step, without requiring any supplementary step. Thus, the knit according to the invention can be manufactured simply and quickly. The knit according to the invention can thus be produced industrially.

Each loop produced on guide-bar B4 of the knit according to the invention is cut as a consequence of its melting and thus gives rise to two barbs protruding outwards from the face on which the loop is present.

Furthermore, melting the monofilament loops makes it possible to obtain barbs having a head with dimensions greater than the diameter of the monofilament, said head thus being well suited to its functions of gripping and fixing, either to biological tissues or to other textiles, in particular porous textiles.

The yarns used to manufacture the knit according to the invention are yarns of biocompatible material which may or may not be bioresorbable.

In the present application, "biocompatible" is understood as meaning that the materials having this property can be implanted in the human or animal body.

All biocompatible materials may be synthetic or natural, biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Non-biodegradable materials suitable for the yarns of the knit of the present invention include polyolefins, such as polyethylene, polypropylene, copolymers of polyethylene and polypropylene, and blends of polyethylene and polypropylene; polyamides, such as nylon; polyamines, polyimines, polyesters such as polyethylene terephthalate (PET), polytetrafluoroethylene, polyether-esters such as polybutesters, polytetramethylene ether glycol; 1,4-butanediol; polyurethanes, and combinations thereof. In embodiments, non-biodegradable materials may include silk, collagen, cotton, linen, carbon fibers, and combinations thereof. The polypropylene may be isotactic polypropylene or a mixture of isotactic and syndiotactic or atactic polypropylene.

Biodegradable materials suitable for the yarns of the knit of the present invention include polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these compounds and mixtures thereof.

In embodiments, all biocompatible materials are selected from polyethylene, polypropylene, polyester such as polyethylene terephthalates, polyamide, silicone, polyether ether ketone (PEEK), polyarylether ether ketone (PAEK), polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the yarns threaded in guide-bars B2 and B3, and optionally in guide-bar B1 when it is threaded, are chosen from among monofilament and/or multifilament yarns. The multifilament yarn count may range from about 50 dtex to about 230 dtex. The diameter of the monofilament yarns may range, for example, from about 0.07 to about 0.20 mm. Any yarn made of biocompatible material can be used.

The yarns threaded in guide-bars B1, B2 and B3 may differ or not from one guide-bar to the other. For example, the yarns threaded on guide-bars B2 and B3 may be selected from polyethylene terephthalate, polypropylene, polylactic acid, polyglycolic acid and mixtures thereof. In embodiments, the yarns threaded on guide-bars B2 and B3 are made of the same material, for example polyethylene terephthalate.

In embodiments, the yarns threaded in guide-bars B2 and B3 are monofilaments of polyethylene terephthalate having a diameter of about 0.09 mm.

The monofilament threaded in guide-bar B4 is made of a hot-melt material.

The hot-melt material can be biodegradable or non-biodegradable and can be chosen from among all the materials cited above, these materials being hot-melt materials. Thus, the hot-melt material forming the monofilament yarn threaded in guide-bar B4 can be chosen from among polylactic acid (PLA), polyglycolic acid (PGA), polycaprolactone (PCL), polydioxanone (PDO), trimethylene carbonate (TMC), polyvinyl alcohol (PVA), polyhydroxyalkanoates (PHAs), polyamides, polyesters, polyethylene terephthalate (PET), aramids, expanded polytetrafluoroethylene, polyvinylidene difluoride (PVDF), polybutylene esters such as polybutylene succinate or polybutylene terephthalate (PBT), polyether ether ketone (PEEK), polyolefins (such as polyethylene or polypropylene), copolymers thereof, and mixtures thereof.

In one embodiment, the hot-melt material is biodegradable. It is thus possible to produce a prosthetic knit having temporary gripping zones: in other words, once the prosthetic knit has been colonized by cells after implantation, the barbs, of which the gripping function is no longer needed, resorb naturally.

In embodiments, the hot-melt material forming the monofilament yarn threaded in guide-bar B4 can be chosen from among poly-L-lactic acid (PLA), polyglycolic acid (PGA), polycaprolactone (PCL), polydioxanone (PDO), trimethylene carbonate (TMC), polyvinyl alcohol (PVA), polyhydroxyalkanoates (PHAs), polyamides, polyesters such as polyethylene terephthalate (PET), polytetrafluoroethylene (PTFE), polybutylene esters, polyether ether ketone, polyolefins such as polyethylene (PE) or polypropylene (PP), copolymers thereof, and mixtures thereof.

The hot-melt material forming the monofilament yarn threaded in guide-bar B4 may be chosen among poly-L-lactic acid, polyglycolic acid, trimethylene carbonate, polydioxanone, polycaprolactone and copolymers thereof. For example, the hot-melt material forming the monofilament yarn threaded in guide-bar B4 is poly-L-lactic acid.

In embodiments, the diameter of the monofilament yarn threaded in guide-bar B4 varies from 0.12 to 0.18 mm, preferably is about 0.15 mm. Such diameters make it possible to obtain barbs having a good ability to grip in the biological tissues or in another porous textile.

In embodiments, the yarn threaded in guide-bar B4 is a monofilament of poly-L-lactic acid having a diameter of about 0.15 mm.

The combination of the knitting patterns followed by guide-bars B2, B3 and B4, and optionnally B1, forms an arrangement of yarns leading to a porous knit.

In embodiments, guide-bar B1 is unthreaded. In such cases, guide-bar B1 is not used for producing the knit of the invention. Using only three guide-bars of the knitting machine instead of four allows an easier configuration of the machine. The knitting step is more efficient. In addition, using only three guide-bars of the knitting machine instead of four allows using less weight of material: using less weight of material favors cellular growth properties of the resulting knit.

In other embodiments, guide-bar B1 may be threaded by yarns of biocompatible material following a knitting pattern involving at least two needles. Having a knitting pattern extending on a certain amount of needles, such as at least two needles, for example between two and eight needles, allows conferring elasticity to the knit, in particular in the warp direction. For example, in embodiments, guide-bar B1 may be threaded by yarns of biocompatible material following a knitting pattern identical to that of guide-bar B2 or identical to that of guide-bar B3.

When threaded, the guide-bar B1 may be used for creating an additional pattern inside the knitted structure obtained with guide-bars B2, B3 and B4. Such an additional pattern may be temporary. For example, guide-bar B1 may threaded by yarns of biodegradable biocompatible material following a knitting pattern involving at least two needles and providing a temporary improved strength in the weft direction, such improved strength in the weft direction being present only during the first step of cicatrization after implantation, the porous knit resuming its elasticity in all directions once the biodegradable material threaded in guide-bar B1 is degraded.

The knitting patterns followed by each of guide-bars B2 and B3 produce the arrangement of yarns defining the two faces of said knit and involve at least two needles. Having a knitting pattern extending on a certain amount of needles, such as at least two needles, for example between two and eight needles, allows conferring elasticity to the knit, in particular in the warp direction. Guide-bars B2 and B3 are intended to produce the basic structure of the knit, to which will be attached the barbs which will result from the knitting of the monofilament threaded in guide-bar B4. Guide-bars B2 and B3 are therefore the guide-bars intended to give the knit of the invention its consistence and stability. As a result, the knitted structure produced by guide-bars B2 and B3 may show good mechanical properties and a certain rigidity in order to perform its function of approximating two tissue layers. In embodiments, the knit of the invention may also be used for reinforcing the abdominal wall, alternatively or in combination to its function of approximating two tissue layers.

In embodiments, the knitting patterns followed by each of guide-bars B2 and B3 may therefore involve between two and eight needles, preferably between three and seven needles, more preferably involve between six and seven needles. Alternatively or in combination, the knitting patterns followed by each of guide-bars B2 and B3 may make stitches. Stitches allow providing good mechanical properties, such as good tensile breaking strength, tear strength and suture pull-out strength, to the knit of the invention.

The knitting pattern followed by guide-bar B4 involves at least two needles. In embodiments, the knitting pattern followed by B4 involves between three and six needles, preferably involves between four and five needles. Guide-bar B4 provides the monofilament from which the barbs will originate after cutting of the loops generated by the knitting pattern of guide-bar B4. The monofilament of guide-bar B4 will end up as a discontinuous monofilament once the barbs are created. This monofilament will therefore in the end not significantly affect the elastic properties of the knit, such as the tensile breaking elongation and the tensile elongation under 50 N, in the warp and weft directions.

In embodiments, the knitting pattern followed by each of guide-bars B2 and B3 involves between six and seven needles and the knitting pattern followed by guide-bar B4 involves between four and five needles. The elasticity of the resulting knits, such as the elongation properties of the knit, is therefore good in the warp direction and in the weft direction.

The elasticity of a knit may be observed by measuring its tensile breaking elongation and tensile elongation under 50 N in the warp direction and in the weft direction. The higher the tensile breaking elongation and the higher the tensile elongation under 50 N, the more elastic the knit is. In embodiments, the knit of the invention has a tensile breaking elongation in the warp direction of at least about 50%, preferably of at least about 70%, preferably of at least about 100%, more preferably of about 108%. In embodiments, the knit of the invention has a tensile breaking elongation in the weft direction of at least about 30%, preferably of at least about 40%, preferably of at least about 45%, more preferably of about 49%. In embodiments, the knit of the invention has a tensile elongation under 50N in the warp direction of at least about 30%, preferably of at least about 60%, preferably of at least about 80%, more preferably of about 85%. In embodiments, the knit of the invention has a tensile elongation under 50N in the weft direction of at least about 5%, preferably of at least about 10%, preferably of at least about 15%, more preferably of about 19%.

In embodiments, guide-bars B2 and B3 are each threaded two full, three empty, according to the following knitting pattern according to the standard ISO 11676 (publication year 2014):

B2: 5-6/3-4/1-0/4-3//
B3: 1-0/3-2/5-6/2-3//

Such knitting patterns involve six needles, extend on four rows of stitches and make stitches. The knitted structure produced by guide-bars B2 and B3 is porous and shows a good elasticity in the warp direction and in the weft direction, while showing a good stability and good mechanical properties.

In embodiments, for example with guide-bars B2 and B3 threaded as above, guide-bar B4 is threaded one full, four empty, according to the following knitting pattern according to the standard ISO 11676 (publication year 2014):

B4: 5-4/2-3/0-1/3-2//

Guide-bar B4 is threaded with the monofilament yarns that are first going to give loops by knitting and that will then subsequently give rise to the barbs after the step of melting the loops. Thus, the above knitting pattern of B4 makes it possible to form loops on both faces of the knit.

In other embodiments, guide-bars B2 and B3 are each threaded one full, two empty, according to the following knitting pattern according to the standard ISO 11676 (publication year 2014):

B2: 0-1/3-4/7-6/4-3/0-1/2-1//
B3: 7-6/4-3/0-1/3-4/7-6/5-6//

Such knitting patterns involve seven needles, extend on six rows of stitches and make stitches. The knitted structure produced by guide-bars B2 and B3 is porous and shows a good elasticity in the warp direction and in the weft direction, while showing a good stability and good mechanical properties.

In embodiments, for example with guide-bars B2 and B3 threaded as above, guide-bar B4 is threaded one full, two empty, according to the following knitting pattern according to the standard ISO 11676 (publication year 2014):

B4: 4-3/1-2/0-1/2-1/4-3/2-2//

Guide-bar B4 is threaded with the monofilament yarns that are first going to give loops by knitting and that will then subsequently give rise to the barbs after the step of melting the loops. Thus, the above knitting pattern of B4 makes it possible to form loops on both faces of the knit.

In the various embodiments described above, it is possible to adapt the surface density of the barbs on the faces of the knit, in function of the desired type of gripping, by modifying the number of stiches produced by the knitting pattern.

In step iii), the knit obtained is then heat-set. The heat-setting step allows stabilizing the knit in width and length, in particular in the weft direction and in the warp direction. The heat-setting step may be performed at a temperature ranging from 40° C. to 120° C., for example at 110° C. In embodiments, the temperature at which the heat-setting step is performed is below the melting point of the hot-melt material forming the monofilament threaded in guide-bar B4, preferably at least about 10° C. below said melting point. The knit may be kept under no tension, neither in the warp direction nor in the weft direction, during the heat-setting step.

In step iv), the loops generated by the hot-melt monofilament threaded in guide-bar B4 are cut so as to form the barbs. The loops are cut via melting the monofilament.

In one embodiment of the invention, step iv) is performed by placing each face of said knit on a cylinder that is brought to a temperature that causes the loops to melt so that they are cut in two and and thus form the barbs, as described in WO01/81667. This cutting generates two barbs, each of them having a head with dimensions usually greater than its stem.

A device for carrying out step iv), such as the cylinder to press flat on the face of the knit comprising the loops, is described in the document WO01/81667, for example. Generally, the knit is guided between several unheated rollers in order to confer upon it a movement, at a constant speed, in the direction of a cylinder heated to a temperature T, such that the face of the knit provided with the loops comes into contact with this cylinder.

The temperature T of the cylinder may depend on the melting point of the material forming the monofilaments threaded in guide-bar B4. In particular, the temperature of the cylinder is preferably higher than the melting point of said material, for example from about 30° C. to about 120° C. higher than said melting point. The temperature of the cylinder is also preferably below the boiling point of the material forming the monofilaments threaded in guide-bar B4, for example at least about 20° C. below said boiling point. The temperature of the cylinder is also preferably below the decomposition point of the material forming the monofilaments threaded in guide-bar B4, for example at least about 20° C. below said decomposition point. For example, when the hot-melt material forming the monofilaments threaded in guide-bar B4 is poly-L-lactic acid, the temperature of the cylinder may range from about 180° C. to about 280° C., in embodiments from about 230° C. to about 260° C.

The barbs of the knit thus obtained can protrude from each face substantially perpendicularly with respect to the plane of said face or, alternatively, in one or more planes inclined with respect to said face.

The barbs obtained are particularly efficient for gripping biological tissues, such as muscles, connective tissues, etc. They are particularly efficient for gripping two separated tissue layers and approximating them together when the prosthetic knit of the invention is positioned between said two separated tissue layers.

Alternatively, these barbs may be intended to be entangled in one or more arrangements of yarns, fibres, filaments and/or multifilaments of another prosthetic textile, for example in order to form a composite reinforcing prosthesis.

The knit of the invention may be used in open surgery or in laparoscopic surgery. In embodiments, the barbs of the knit of the invention may be coated by an anti-adhesion coating, for example a collagen coating, to prevent the gripping of the knit on itself when the knit is rolled on itself in order to be introduced into a trocar. In embodiments, one face or both faces (s) of the knit may be partially or totally coated by an anti-adhesion coating, for example a collagen coating, to prevent the gripping of the knit on itself when the knit is rolled on itself in order to be introduced into a trocar. Anti-adhesion coatings and methods for applying them on the barbs and/or faces of the knit of the invention are for example described in EP 2 473 214 B1 and in EP 2 473 133 B1.

The knit of the invention may be used as it is as a two-sides fixation patch for approximating two tissue layers which have been previously separated. An aspect of the invention is therefore a two-sides fixation patch for approximating two tissue layers comprising at least one knit as described above. The use of the knit of the invention further prevents the appearance of the seroma phenomenon.

Alternatively, the knit of the invention may be used on its own or as a part of a prothesis for wall reinforcement in parietal or visceral surgery, in particular for the treatment of hernias. For example, the knit of the invention may be combined with another textile or with two other textiles (one on each face). An aspect of the invention is therefore a prothesis for wall reinforcement in parietal or visceral surgery, in particular for the treatment of hernias, comprising at least one knit as described above.

The knit of the invention may also be used in laparoscopy in combination with a dissection balloon: the combination of the knit of the invention with a dissection balloon may be used for approximating two layers of tissue directly by themselves at the end of surgery, at the time the balloon is exsufflated. The use of the knit of the invention may prevent the appearence of seroma.

BRIEF DESCRIPTION OF THE DRAWINGS

The invention will be better understood from the following detailed description and examples, and also from the figures, in which.

EXAMPLE 1

A prosthetic knit according to the invention is produced on a warp knitting machine with four guide bars B1, B2, B3 and B4, as described above, where the bar B1 is in position 1 on the knitting machine, the bar B2 is in position 2, the bar B3 is in position 3, and the bar B4 is in position 4.

Guide-bar B1 is unthreaded.

Guide-bars B2 and B3 are threaded two full, three empty, according to the following knitting pattern according to the standard ISO 11676 (publication year 2014):

B2: 5-6/3-4/1-0/4-3//
B3: 1-0/3-2/5-6/2-3//

And Guide-bar B4 is threaded one full, four empty, according to the following knitting pattern according to the standard ISO 11676 (publication year 2014):

B4: 5-4/2-3/0-1/3-2//

The yarns threaded in guide-bars B2 and B3 are monofilaments made of polyethylene terephthalate (PET) having a diameter of 0.09 mm.

The yarns threaded in guide-bar B4 are monofilaments of poly-L-lactic acid (PLLA) having a diameter of 0.15 mm.

DETAILED DESCRIPTION OF EMBODIMENTS

Figure 1A:
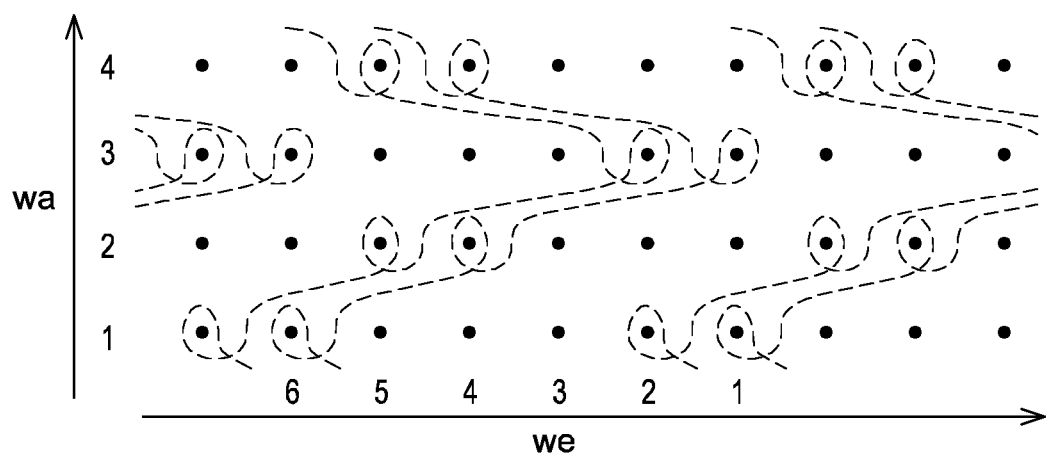
FIG. 1A is a schematic view of a knitting pattern suitable for guide-bar B2 of the method and knit of the invention.
Figure 1B:
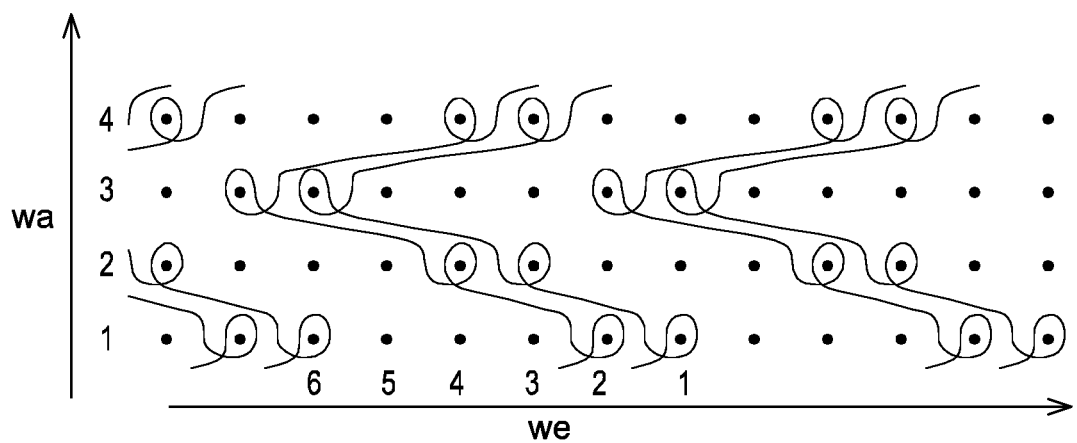
FIG. 1B is a schematic view of a knitting pattern suitable for guide-bar B3 of the method and knit of the invention.
Figure 1C:
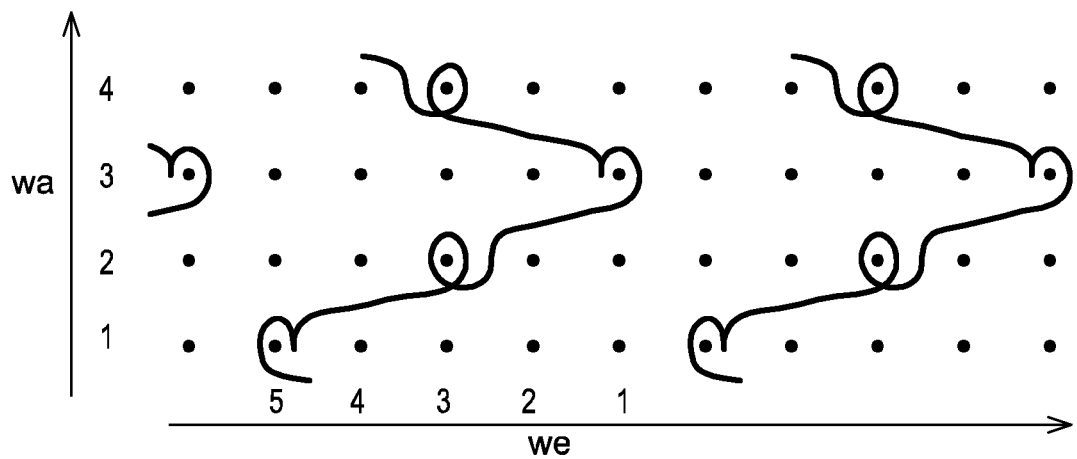
FIG. 1C is a schematic view of a knitting pattern suitable for guide-bar B4 of the method and knit of the invention.

The respective knitting patterns for B2, B3 and B4 are illustrated in FIGS. 1A to 1C in a representation well known to a person skilled in the art, where «wa» indicates the warp direction and «we» indicates the weft direction. For each Figure, the graphic shows the movement of the guide-bar. The guide-bars' movement is read from bottom to top, the first knitted course being at the bottom.

As appears on these figures, six needles (numbered from 1 to 6 on the figures) are used for each knitting pattern of B2 and B3. A set of five needles (numbered from 1 to 5 on the figure) is used for the knitting pattern of B4.

Figure 2:
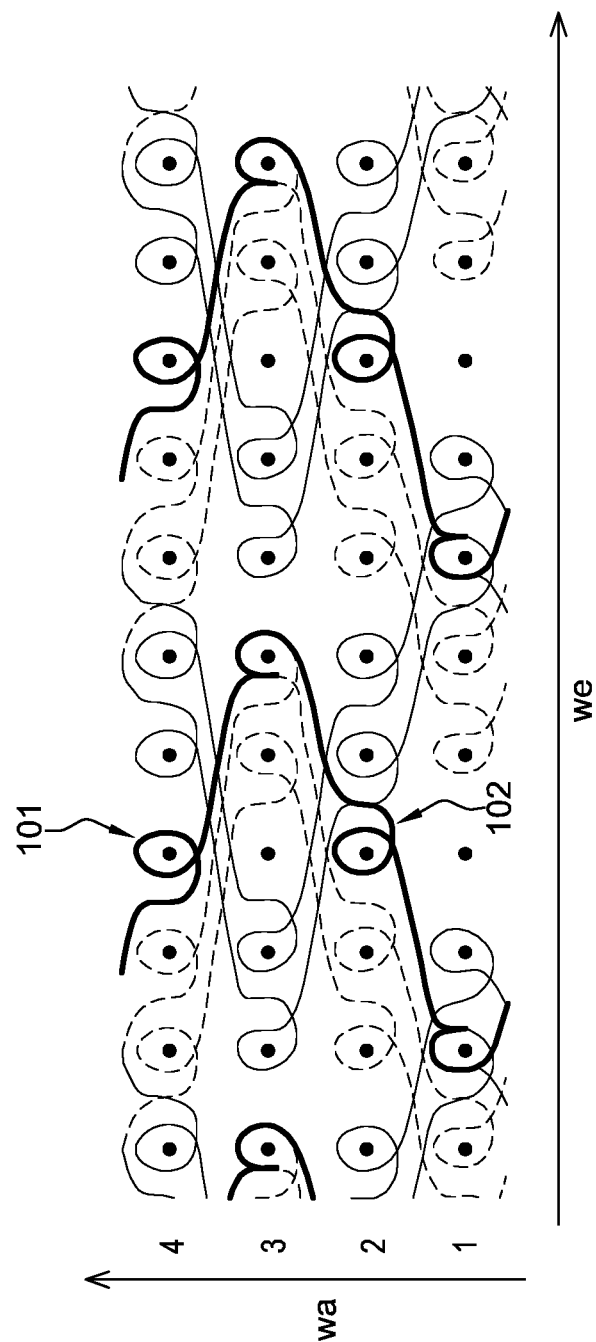
FIG. 2 is a schematic view of the knitting patterns of FIGS. 1A-1C shown together, permitting production of a knit according to the invention.

In FIG. 2 is illustrated the combination of the three knitting patterns indicated by a fine line for B2, by a dot-and-dash line for B3, and by a solid line for B4, where «wa» indicates the warp direction and «we» indicates the weft direction.

The yarns threaded in B2 and B3 constitute the base of the knit of the present knit, since the hot-melt monofilament yarn, intended to generate the barbs, will be regularly cut during the melting step. The knitting patterns of guide-bars B2 and B3 produce an arrangement of yarns defining the two faces of the knit. They make stitches.

The combination of the knitting patterns, as described in this example, makes it possible to directly produce, by knitting, a porous knit which, on each of its two faces, has loops capable of giving rise to outwardly protruding barbs.

On FIG. 2 are shown two stitches 101 and 102 produced by guide-bar B4. Stitch 101 is for example the stitch produced on a first side of the knit, that will generate a loop on said first side of the knit, and further on barbs, after melting of the loop. Stitch 102 is the stitch produced on the opposite side of the knit that will generate a loop on said opposite side of the knit, and further on barbs, after melting of the loop.

Once the knit has been produced as indicated above, it is heat-set, for example at 110° C., in order to stabilize it in length and width.

After the heat-setting step, each face of the knit is placed in contact with a cylinder containing an electrical heating resistor so as to melt the loops present on said face.

In the present example, the melting point of poly-L-lactic acid being 165° C., the cylinder is heated at a temperature T of 250° C.

On melting, each loop produced by monofilaments of guide-bar B4 cuts in two and gives rise to two barbs protruding outwards from the face of the knit, each barb preferably having a head with dimensions greater than those of the diameter of the monofilament yarn forming the initial loop.

The following properties of the knit of the invention of the present example have been determined as follows:

Linear density (g/m$^2$): measured according to ISO 3801: 1977 «Determination of mass per unit length and mass per unit area», 5 samples, 1 dm$^2$ disk, pore size (width×height) (mm): knit biggest pores width and height are measured making one measurement on 5 individual samples of dimensions 100×50 mm, with a profile projector such as a projector, Thickness: is measured according to ISO 9073-2: 1997 "Textiles—test methods for nonwovens—Part 2: Determination of thickness", method used for voluminous nonwovens with a thickness less than 20 mm, 10 samples, 100×50 mm, Tensile strength (N), tensile elongation (%) and elongation under 50 N (%): are measured according to ISO 13934-1: 1999 "Determination of breaking strength and elongation", 5 samples, width: 50 mm, length: 200 mm between the jaws, Crosshead speed: 100 mm/min, Pre-load: 0.5 N, using a traction testing machine such as the Hounsfield model H5KS (Hounsfield, Redhill, England), Bursting strength (kPa): measured according to ISO 13938-2: 1999 "Textiles—Bursting properties of fabrics—Pneumatic method for determination of bursting strength and bursting deformation", 5 samples using a Bursting strength tester, heal model Truburst, Suture pull out strength in the warp direction and in the weft direction measured as follows: a USP 2 suture yarn is passed through a pore of a 50×100 mm sample, at 10 mm from the edge of a small side of the sample, and is tracted away using a traction testing machine such as the Hounsfield model H5KS (Hounsfield, Redhill, England) with the following conditions: 5 samples, width 50 mm, 100 mm between the jaws, crosshead speed: 100 mm/min, Tear strength (N) in the warp direction and in the weft direction: measured according to superseded ISO 4674:1977 "Determination of tear resistance of coated fabrics" Method A2, 5 samples, width: 75 mm, Tear length≤145 mm, crosshead speed: 100 mm/min.

The results are collected in the following table:

TABLE I properties of the knit

| Property | Knit of present example | |
|---|---|---|
| Surface density (g/m$^2$) | 87 | |
| Thickness (mm) | 4.1 | |
| Pore size (mm$^2$) (width × height) | 1.7 × 1.6 | |
| Bursting strength (kPa) | 132 ± 8 | |
| | Warp | Weft |
| Tensile breaking strength (N) | 112 ± 8 | 239 ± 6 |
| Tensile breaking elongation (%) | 108 ± 6 | 49 ± 1 |
| Tensile Elongation under 50N (%) | 85 ± 2 | 19 ± 1 |
| Tear strength (N) | 29 ± 2 | 27 ± 3 |
| Suture pull-out strength (N) | 41 ± 4 | 35 ± 4 |

The knit of the invention of the present example therefore shows a tensile breaking elongation of 108% in the warp direction and a tensile breaking elongation of 49% in the weft direction. This knit further shows a tensile elongation under 50 N of 85% in the warp direction and a tensile elongation under 50 N of 19% in the weft direction.

The knit of the present example is therefore particularly adapted for approximating two tissue layers that have been previously separated, by gripping one tissue layer via the barbs of one of its faces, and gripping the other tissue layer via the barbs of its other face. Thanks to the elongation properties of the knit, the approximated tissue layers are free to move with respect to each other, while being firmly attached to each other, thereby being capable of smoothly adapting to pressures of various directions and intensities generated by the movements of a patient in its daily life.

Such a knit can be used as it is, directly as a two-sides fixation patch for approximating two tissue layers which have been previously separated or as a prosthesis in parietal or visceral surgery for wall reinforcement. Alternatively, this knit can be combined with another textile, with two textiles (one on each face), or with an anti-adhesion film on one or both of its faces. The barbs can be covered with an anti-adhesion coating to prevent them from becoming entangled in the body of the knit when the latter is folded up on itself, for example in order to be introduced into a trocar.

The knit of the present example further allows preventing the apearance of seroma subsequent to surgery.

EXAMPLE 2 (COMPARATIVE)

A comparative knit, having barbs protruding outwards from both faces, has been manufactured according to the following method: the comparative knit is produced on a warp knitting machine with four guide bars B1, B2, B3 and B4, where the bar B1 is in position 1 on the knitting machine, the bar B2 is in position 2, the bar B3 is in position 3, and the bar B4 is in position 4.

Guide-bar B1 is threaded one full, three empty according to the following knitting pattern according to the standard ISO 11676 (publication year 2014):

B1: 2-3/2-1/1-0/1-2//

Guide-bar B2 is threaded one full, one empty according to the following knitting pattern according to the standard ISO 11676 (publication year 2014):

B2: 1-0/0-1//

The knitting pattern of guide-bar B2 therefore involves only one needle.

Guide-bar B3 is threaded one full, one empty according to the following knitting pattern according to the standard ISO 11676 (publication year 2014):

B3: 1-0/5-5/1-0/3-3//

Guide-bar B4 is threaded one full, three empty according to the following knitting pattern according to the standard ISO 11676 (publication year 2014):

B4: 2-1/5-5/3-4/0-0//

The yarns threaded in guide-bars B2 and B3 are monofilaments made of polyethylene terephthalate (PET) having a diameter of 0.09 mm.

The yarns threaded in guide-bars B1 and B4 and intended to generate the barbs are monofilaments of poly-L-lactic acid (PLLA) having a diameter of 0.15 mm.

The tensile breaking elongation and the tensile elongations under 50 N in the warp direction and in the weft direction have been measured for the comparative knit according to the methods described at Example 1.

The results are collected in the following table:

TABLE II comparison of elongation parameters between a knit of the invention and a comparative knit

| Property | Comparative knit of Example 2 | | Knit of Example 1 | |
|---|---|---|---|---|
| | Warp | Weft | Warp | Weft |
| Tensile breaking elongation (%) | 45 ± 4 | 108 ± 8 | 108 ± 6 | 49 ± 1 |
| Tensile Elongations under 50N (%) | 12 ± 2 | 45 ± 2 | 85 ± 2 | 19 ± 1 |

As appears from these results, the knit of the invention shows a tensile breaking elongation in the warp direction more than two times higher than that of the comparative knit. The knit of the invention further shows tensile elongation under 50 N in the warp direction more than six times higher than that of the comparative knit.

The knit of the invention is therefore particularly adapted to conform to the variations of intensity and of direction of pressures in the anatomy of a person subsequent to the movements of this person during his daily life.

What is claimed is:

1. A method for manufacturing a prosthetic porous knit comprising an arrangement of yarns of biocompatible material defining at least two faces of the knit, said knit provided with barbs protruding outwards from each of the at least two faces, said method comprising:
   i) providing a warp knitting machine comprising one needle-bed comprising a first guide-bar B1, a second guide-bar B2, a third guide-bar B3, and a fourth guide-bar B4,
   ii) knitting yarns of biocompatible material on the warp knitting machine to form the knit, wherein:
      the first guide-bar B1 is either unthreaded or threaded with the yarns of biocompatible material and follows a knitting pattern involving at least two needles,
      the second guide-bar B2 and the third guide-bar B3 are threaded with the yarns of biocompatible material and follow knitting patterns involving at least two needles and producing the arrangement of yarns defining the at least two faces of the knit,
      the fourth guide-bar B4 is threaded with a hot-melt monofilament yarn of biocompatible material and follows a knitting pattern making stitches generating loops protruding outwards from each of the at least two faces of the knit,
   iii) heat-setting the knit obtained at ii),
   iv) forming barbs by melting the loops.

2. The method according to claim 1, wherein the knitting patterns each followed by the second guide-bar B2 and the third guide-bar B3 involve between two and eight needles.

3. The method according to claim 1, wherein the knitting patterns each followed by the second guide-bar B2 and the third guide-bar B3 involve between three and seven needles.

4. The method according to claim 1, wherein the knitting patterns each followed by the second guide-bar B2 and the third guide-bar B3 involve between six and seven needles.

5. The method according to claim 1, wherein the knitting patterns each followed by the second guide-bar B2 and the third guide-bar B3 make stitches.

6. The method according to claim 1, wherein the knitting pattern followed by the fourth guide-bar B4 involves between three and six needles.

7. The method according to claim 1, wherein the knitting pattern followed by the fourth guide-bar B4 involves between four and five needles.

8. The method according to claim 1, wherein the first guide-bar B1 is unthreaded.

9. The method according to claim 1, wherein the second guide-bar B2 and the third guide-bar B3 are each threaded two full, three empty, according to the following knitting pattern:

B2: 5-6/3-4/1-0/4-3//
B3: 1-0/3-2/5-6/2-3//.

10. The method according to claim 9, wherein the fourth guide-bar B4 is threaded one full, four empty, according to the following knitting pattern:

B4: 5-4/2-3/0-1/3-2//.

11. The method according to claim 1, wherein the second guide-bar B2 and the third guide-bar B3 are each threaded one full, two empty, according to the following knitting pattern:

B2: 0-1/3-4/7-6/4-3/0-1/2-1//
B3: 7-6/4-3/0-1/3-4/7-6/5-6//.

12. The method according to claim 11, wherein the fourth guide-bar B4 is threaded one full, two empty, according to the following knitting pattern:

B4: 4-3/1-2/0-1/2-1/4-3/2-2//.

13. The method according to claim 1, wherein the hot-melt material forming the monofilament yarn threaded in the fourth guide-bar B4 is poly-L-lactic acid.

14. The method according to claim 1, wherein the diameter of the monofilament yarn threaded in the fourth guide-bar B4 varies from 0.12 to 0.18 mm.

15. The method according to claim 1, wherein yarns threaded on the second guide-bar B2 and the third guide-bar B3 are made of polyethylene terephthalate.

16. The method according to claim 1, wherein the knit displays a tensile breaking elongation in a warp direction of at least 50%.

17. The method according to claim 16, wherein the tensile breaking elongation in the warp direction is at least 70%.

18. The method according to claim 16, wherein the tensile breaking elongation in the warp direction is at least 100%.

19. A prosthetic porous knit made from the method of claim 1.

* * * * *